(12) United States Patent
Greene et al.

(10) Patent No.: US 9,976,207 B2
(45) Date of Patent: *May 22, 2018

(54) SINGLE STEP SHAPE MEMORY ALLOY EXPANSION

(71) Applicant: W. L. Gore & Associates, Inc., Newark, DE (US)

(72) Inventors: Joel M. Greene, Flagstaff, AZ (US); Christopher C. Lasley, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/243,620

(22) Filed: Aug. 22, 2016

(65) Prior Publication Data
US 2016/0355912 A1   Dec. 8, 2016

Related U.S. Application Data

(63) Continuation of application No. 13/235,319, filed on Sep. 16, 2011, now Pat. No. 9,422,615.

(51) Int. Cl.
| | |
|---|---|
| F03G 7/06 | (2006.01) |
| C22F 1/00 | (2006.01) |
| C22F 1/10 | (2006.01) |
| A61F 2/915 | (2013.01) |
| A61F 2/01 | (2006.01) |
| A61F 2/24 | (2006.01) |

(Continued)

(52) U.S. Cl.
CPC ............... *C22F 1/006* (2013.01); *A61F 2/01* (2013.01); *A61F 2/2418* (2013.01); *A61F 2/844* (2013.01); *A61F 2/915* (2013.01); *B23H 9/005* (2013.01); *B23K 26/38* (2013.01); *C22F 1/10* (2013.01); *C23F 1/04* (2013.01); *F03G 7/065* (2013.01); *A61F 2002/018* (2013.01); *A61F 2210/0014* (2013.01); *A61F 2210/0019* (2013.01); *A61F 2230/0054* (2013.01); *A61F 2240/001* (2013.01); *A61F 2310/00023* (2013.01); *B23K 2203/08* (2013.01)

(58) Field of Classification Search
CPC ............... F03G 7/00; F03G 7/06; F03G 7/065
USPC .......... 60/527–529; 623/1.11–1.19; 29/33 D, 29/DIG. 41
See application file for complete search history.

(56) References Cited

U.S. PATENT DOCUMENTS

| | | |
|---|---|---|
| 5,876,445 A | 3/1999 | Andersen |
| 5,907,893 A | 6/1999 | Zadno-Aziz et al. |

(Continued)

FOREIGN PATENT DOCUMENTS

WO   WO-2007134321 A2   11/2007

OTHER PUBLICATIONS

International Search Report and Written Opinion for PCT/US2012/055349 mailed Jan. 23, 2013, corresponding to U.S. Appl. No. 13/235,319.

(Continued)

*Primary Examiner* — Laert Dounis

(57) ABSTRACT

Exposing nitinol to a shape setting temperature while the nitinol is in an unstrained or minimally strained condition. The nitinol is then substantially deformed in shape while at elevated temperature. After deformation, the nitinol remains at the elevated temperature for a time to shape set the material. The nitinol is then returned to approximately room temperature 20° C. by means of water quenching or air cooling for example.

12 Claims, 7 Drawing Sheets

(51) Int. Cl.
*A61F 2/844* (2013.01)
*B23H 9/00* (2006.01)
*B23K 26/38* (2014.01)
*C23F 1/04* (2006.01)
*B23K 103/08* (2006.01)

(56) References Cited

U.S. PATENT DOCUMENTS

| | | |
|---|---|---|
| 9,422,615 B2 | 8/2016 | Greene |
| 2004/0216814 A1 | 11/2004 | Dooley et al. |
| 2007/0288034 A1 | 12/2007 | MacCollum et al. |
| 2007/0288080 A1 | 12/2007 | Maccollum et al. |
| 2007/0293939 A1 | 12/2007 | Shrivastava et al. |
| 2009/0151416 A1 | 6/2009 | Obradovic et al. |
| 2009/0282669 A1 | 11/2009 | von Oepen et al. |

OTHER PUBLICATIONS

Poncin et al. Nitinol self-expanding tubular devices: A tool to select the proper tubing size for the needs of the application. SMST 2000 Conference Proceedings, pp. 477-486.

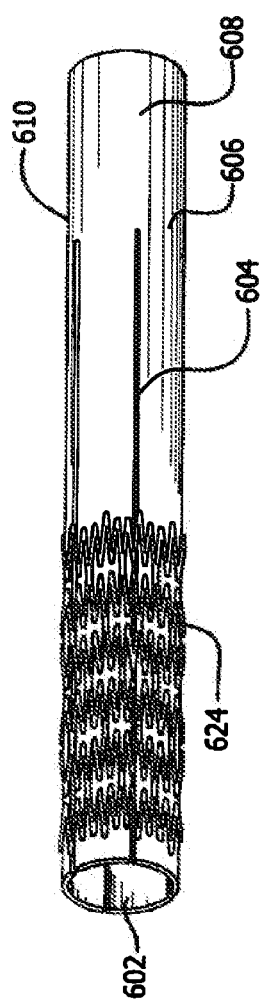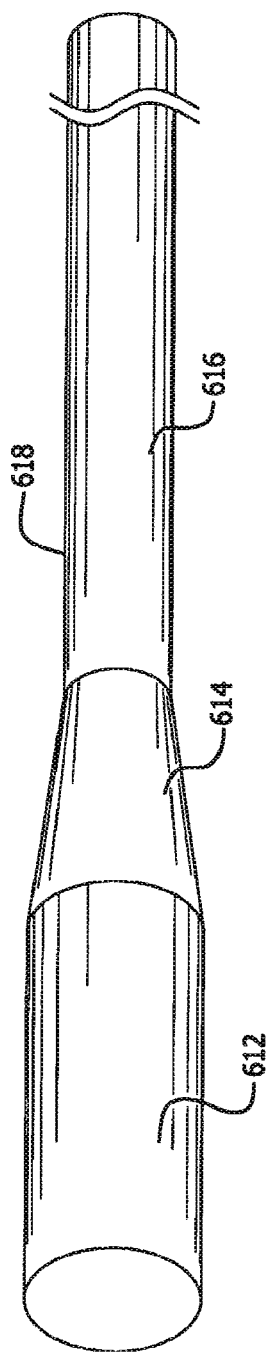
FIG. 6A
FIG. 6B

SINGLE STEP SHAPE MEMORY ALLOY EXPANSION

CROSS-REFERENCE TO RELATED APPLICATION(S)

This application is a continuation of U.S. application Ser. No. 13/235,319, filed Sep. 16, 2011 (issuing as U.S. Pat. No. 9,422,615 on Aug. 23, 2016), which is incorporated herein by reference in its entirety.

BACKGROUND OF THE INVENTION

It is well known to employ various intravascular endoprostheses delivered percutaneously for the treatment of diseases of various body vessels. These types of endoprostheses are commonly referred to as stents. A stent is generally a tubular device formed of a biocompatible material such as nitinol. The fabrication of stents from nitinol tubes that are cut by such methods as laser cutting, water jet cutting, electrical discharge maching, and chemical milling is commonly known. Nitinol is considered a shape memory alloy (SMA). Nitinol also has a shape setting temperature, defined as any temperature within the temperature range at which a shape memory alloy (SMA) article, when exposed to for a period of time in a constrained shape, will substantially maintain the constrained shape when the article is subsequently unconstrained.

The manufacturing of nitinol tubes is expensive. The larger the diameter of the nitinol tube the more expensive it becomes. The cost constraints of large diameter nitinol tubing have resulted in the practice of cutting patterns (such as stent patterns) into small diameter nitinol tubes and then incrementally expanding and shape setting these tubes to attain larger diameter nitinol tubes (and/or nitinol stents).

One general method of shape setting nitinol involves deforming and constraining the nitinol in a desired shape at room temperature (usually about 20° C.) or at below room temperature. The nitinol is then exposed to an elevated temperature (usually about 500° C.) while constrained in a desired shape, in a furnace for example, for a period of time (usually about 5 to 20 minutes). The nitinol is then cooled to room temperature by either water quenching or allowing the nitinol to air cool. This shape setting process imparts a new shape to the nitinol. The new shape is a result of the specific prior deformation and constraining of the cut tube.

In the case of expansion of a cut nitinol tube, a series of incremental expansion and shape setting steps are commonly used. The traditional method for nitinol stent device manufacturing is described by Poncin et. al. (SMST-2000 Conference Proceedings, pp 477-486) which states "[t]he device is expanded to its final size by a succession of progressive, shape-setting steps involving heat treatments." Using a series of incremental expansion steps reduces the incidence of fracture or cracking of the cut nitinol tube during shape setting.

In one example, a stent pattern can be laser cut into a nitinol tube having an outer diameter of about 4 mm. In order to expand this 4 mm cut tube to a 24 mm cut tube, a series of incremental expansion steps would be taken. For example: the cut nitinol tube would be expanded from a 4 mm diameter to an 8 mm diameter and then shape set; next, the cut nitinol tube would then be expanded from 8 mm to 12 mm diameter and then shape set; and so on until the desired 24 mm diameter cut tube is attained.

It is common practice to utilize a series of expansion steps in stent forming to avoid stent fracture during the shape setting process. The above example utilized five expansion steps to attain the desired stent diameter of 24 mm. Omitting even one of these expansion steps, expanding from 4 mm to 12 mm and shape setting for example, can result in the stent fracturing during shape setting. This process of forming nitinol incrementally through a series of shape setting steps is costly and time consuming.

It is also common practice for those skilled in the art to cool nitinol stents, forming thermally induced martensite prior to the expansion of a nitinol tube. Nitinol tubes that are primarily austenite at room temperature will be easier to deform and diametrically expand if they are first cooled to form thermally induced martensite. Because martensitic nitinol is easier to deform than austenitic nitinol, it has been assumed that forming thermally induced martensite prior to expanding a nitinol tube will minimize crack formation in the stent. In spite of this practice of thermally inducing martensite prior to nitinol tube expansion, crack formation during expansion of nitinol tubes is a problem. The practice of thermally inducing martensite prior to nitinol tube expansion has not eliminated the need for incremental expansion steps required to diametrically expand and shape set nitinol tube.

Therefore, there has been a need to have a nitinol medical device forming process that overcomes the disadvantages of the prior art. The present invention provides such a solution.

SUMMARY OF THE INVENTION

In accordance with the present invention, there is provided a method of forming nitinol. In one embodiment, nitinol is exposed to a shape setting temperature of at least 300° C. to about 650° C. in an unstrained or minimally strained condition. The nitinol is then substantially deformed in shape while at this elevated temperature. After deformation, the nitinol is retained at the elevated temperature while constrained in the desired shape for a time to shape set the material. In another embodiment, the nitinol may be deformed once or more than once while at the elevated temperature. The nitinol is then returned to approximately room temperature (about 20° C.), by means of water quenching and/or air cooling for example while still being constrained.

Thus, one embodiment of the invention comprises a method of forming a shape memory alloy (SMA) article, comprising, providing a SMA article having an initial shape, said SMA having a shape setting temperature, heating the SMA article to about said shape setting temperature, deforming the SMA article while at about its shape setting temperature to a final shape, and cooling the SMA article while being constrained thereby substantially retaining said final shape. In one embodiment, after deforming said SMA article while at about its shape setting temperature, allowing said deformed SMA article to dwell while at about its shape setting temperature. In another embodiment, said shape setting temperature is about 300° C. to about 650° C. In another embodiment, said SMA is nitinol. In another embodiment, deforming said SMA article into said final shape is accomplished by application of an internal force. In another embodiment, deforming said SMA article into said final shape is accomplished by application of an external force. In another embodiment, said deforming SMA article into said final shape is accomplished by use of a tapered mandrel. In another embodiment, said SMA article is shaped into a medical device. In another embodiment, said medical device is an implantable device. In another embodiment, said implantable device is selected from the group consisting of a stent, cardiac occluder, valve, and an intraluminal filter. In another embodiment, said SMA initial shape was formed by machining. In another embodiment, said machining comprises laser cutting, water jet cutting, electrical discharge machining, and/or chemical etching.

Another embodiment of the invention comprises a method of forming a stent, comprising, providing a machined shape memory alloy (SMA) tube, wherein said machined SMA tube comprises: a stent pattern, a first (smaller) diameter, and a shape setting temperature, heating said machined SMA tube to about said shape setting temperature, deforming said machined SMA tube while at about its shape setting temperature to a second (larger) diameter and cooling the SMA article while being constrained thereby substantially retaining said second diameter. In one embodiment, said machining comprises laser cutting, water jet cutting, electrical discharge machining and/or chemical etching. In another embodiment, said stent pattern comprises a sinusoidal shape, a diamond shape, a U shape, a V shape or an ovaloid shape. In another embodiment, said SMA tube has a circular cross-section. In another embodiment, after deforming said SMA tube while at about its shape setting temperature, allowing said deformed SMA tube to dwell. In another embodiment, said shape setting temperature is about 300° C. to about 650° C. In another embodiment, deforming said SMA tube into said second shape is accomplished by application of an internal force. In another embodiment, deforming said SMA tube into said second shape is accomplished by application of an external force. In another embodiment, said deforming SMA tube into said second shape is accomplished by use of a tapered mandrel. In another embodiment, the ratio of the second (larger) diameter shape to the first (smaller) diameter shape is greater than about 1.25:1 In another embodiment, the ratio of the second (larger) diameter shape to the first (smaller) diameter shape is greater than about 1.5:1. In another embodiment, the ratio of the second (larger) diameter shape to the first (smaller) diameter shape is greater than about 2:1. In another embodiment, the ratio of the second (larger) diameter shape to the first (smaller) diameter shape is greater than about 3:1. In another embodiment, the ratio of the second (larger) diameter shape to the first (smaller) diameter shape is greater than about 4:1.

In another embodiment, the invention comprises a medical device, comprising a shape memory alloy (SMA) article tailored to transition between a first, second and third state, wherein said SMA comprises a shape setting temperature, wherein, the article in a first state comprises a first circumferential perimeter, the article in a second state comprises multiple circumferential perimeters, the article in a third state comprises a third circumferential perimeter, wherein each of said second state circumferential perimeters are larger than the first state circumferential perimeter and smaller than the third state circumferential perimeter and wherein the shape memory alloy (SMA) article is kept at said shape setting temperature while transitioning between the first, second and third states.

Another embodiment of the invention comprises a device for deforming a SMA article, comprising a slotted elongated tube comprising; i. a longitudinal axis and a first outer perimeter, ii. the tube having a length, a through lumen and a wall, iii. the lumen defining a first inner perimeter, iv. the tube having at least two slots through the wall, v. the slots being oriented essentially parallel to the tube longitudinal axis, vi. the slots extending partially along the tube length; an expansion mandrel comprising, i. a first portion with an essentially constant first perimeter, ii. a second tapered portion, iii. the second tapered portion having a varying perimeter transitioning from the mandrel first perimeter to a larger second perimeter, iv. the mandrel first portion perimeter being dimensioned to be inserted into the lumen first inner perimeter of said slotted elongated tube; and a shape memory alloy article surrounding at least a portion of said slotted elongated tube. In one embodiment, said SMA is nitinol. In another embodiment, said SMA article is a medical device. In another embodiment, said medical device is selected from the group consisting of a stent, cardiac occluder, valve, and an intraluminal filter.

Another embodiment of the invention comprises a device for deforming a SMA article, comprising a slotted elongated tube comprising, i. a longitudinal axis and a first outer perimeter, ii. the tube having a length, a through lumen and a wall, iii. the lumen defining a first inner perimeter, iv. the tube having at least two slots through the wall, v. the slots being oriented essentially parallel to the tube longitudinal axis, vi. the slots extending partially along the tube length; an expansion mandrel comprising, i. a first portion with an essentially constant first perimeter, ii. a second tapered portion, iii. the second tapered portion having a varying perimeter transitioning from the mandrel first perimeter to a larger second perimeter, iv. the mandrel first portion perimeter being dimensioned to be inserted into the lumen first inner perimeter of said slotted elongated tube; wherein the slotted elongated tube surrounds at least a portion of the expansion mandrel and a SMA article surrounding at least a portion of said slotted elongated tube. In one embodiment, the slotted elongated tube surrounds at least a portion of the expansion mandrel first portion. In another embodiment, the slotted elongated tube surrounds at least a portion of the expansion mandrel second tapered portion. In another embodiment, the expansion mandrel further comprises a third portion having an essentially constant second perimeter. In another embodiment, the slotted elongated tube surrounds at least a portion of the expansion mandrel third portion.

Another embodiment of the invention comprises a device for deforming a shape memory alloy (SMA) article, comprising, a slotted elongated tube comprising, i. a longitudinal axis and a first outer perimeter, ii. the tube having a length, a through lumen and a wall, iii. the lumen defining a first inner perimeter, iv. the tube having at least two slots through the wall, v. the slots being oriented essentially parallel to the tube longitudinal axis, vi. the slots extending partially along the tube length, vii. the tube having a first portion with an essentially constant first perimeter, viii. the tube having a second tapered portion, ix. the second tapered portion having a varying perimeter transitioning from the tube first perimeter to a larger second perimeter; and a translating device comprising, i. a rod sized to extend and slide through the slotted elongate tube through lumen, ii. the rod having at least two fins sized to extend and slide through said slots through the wall of the slotted elongated tube, a SMA article surrounding at least a portion of said slotted elongated tube.

Thus, in accordance with the methods of present invention, a nitinol tube (e.g. a stent) can be expanded to a much larger diameter (e.g. 6× or more) in a single processing step.

BRIEF DESCRIPTION OF THE DRAWINGS

The exemplary embodiments of the present invention will be described in conjunction with the accompanying drawings in which, where appropriate, like numerals denote like elements and are offset by 100. The accompanying drawings are included to provide a further understanding of the invention and are incorporated in and constitute a part of this specification, illustrate embodiments of the invention and together with the description serve to explain the principles of the invention.

FIG. 6A is a perspective view of a slotted tube of the present invention.

FIG. 6A is a perspective view of a slotted tube of the present invention and an unexpanded stent.

FIG. 6B is a perspective view of a tapered mandrel of the present invention.

DETAILED DESCRIPTION OF THE INVENTION

As currently known in the art, nitinol tubes having various diameters and wall thicknesses can be cut to form a desired pattern, such as a stent pattern. The cut tube may be placed onto an expansion fixture and expanded by about 20% while at ambient temperature. The cut tube and the expansion fixture may be then heated to an elevated temperature and after an appropriate dwell time, the cut tube and fixture can be quenched to return the cut tube to an ambient temperature. This process may be repeated with each cycle expanding the tube an additional about 20% resulting in a desired diameter (i.e. 100% expansion).

Figure 1:
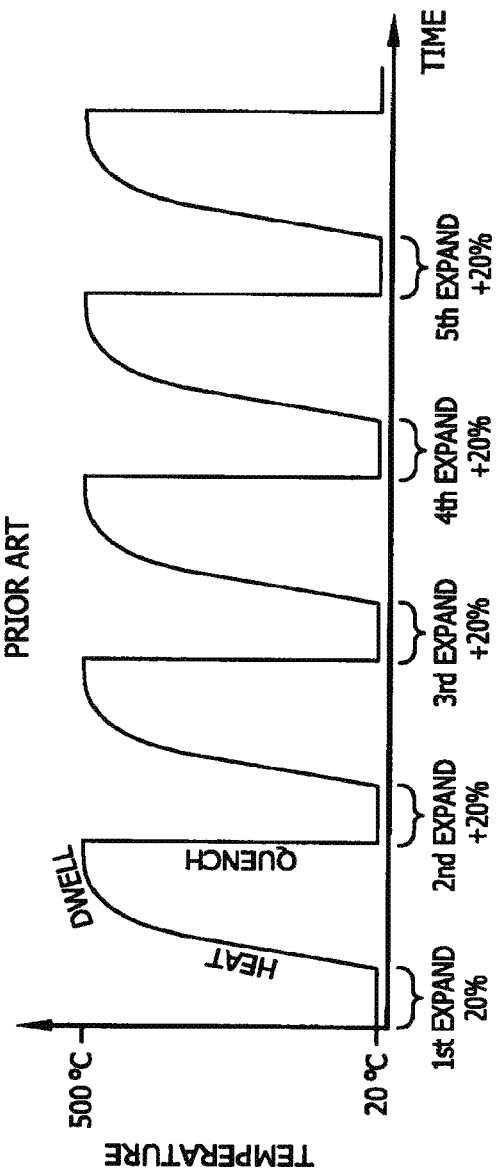
FIG. 1 is a Time/Temperature graph displaying a multi-step heat forming process as currently known in the art.

Shown in FIG. 1 is a Time/Temperature graph displaying a typical expansion process as commonly known in the art. In this example, a five step expansion process is shown, wherein each expansion occurs at about ambient temperature (about 20° C.). Each of the five expansion steps expands the cut tube by about 20% of its expanded diameter. After each expansion, the cut tube and expansion fixture are heated to about 500° C. and after an appropriate dwell, the cut tube and expansion fixture are water quenched, returning the cut tube and expansion fixture to ambient temperature. As shown, the process is repeated four additional times, resulting in a desired diameter (total expansion of about 100%).

Figure 2:
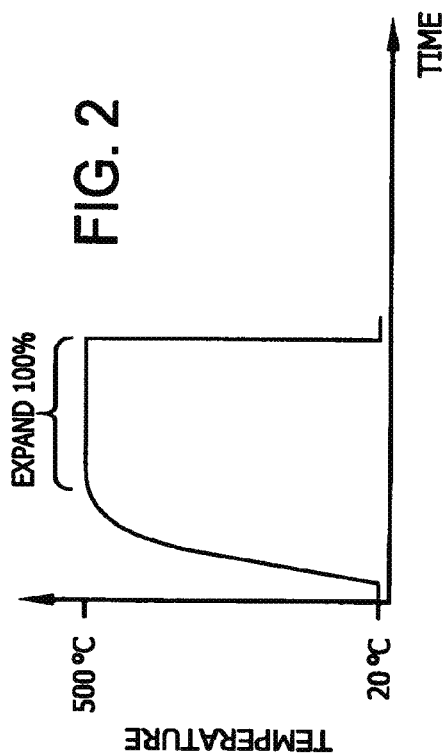
FIG. 2 is Time/Temperature graph displaying a single-step heat forming process according to the present invention.

FIG. 2 is a graph (having the same axes as FIG. 1), depicts a process that expands a cut tube to the desired diameter (i.e. about 100% expansion) in a single expansion step. As shown in FIG. 2, a cut tube is placed onto an expansion fixture. The cut tube and the expansion fixture can then be heated to an elevated temperature and while at this elevated temperature, the expansion fixture can be activated to expand the cut tube by about 100% in a single expansion step. In another embodiment, said expansion fixed can be activated to expand the cut tube by about 200%, about 300%, about 400% and/or about 500%. By comparing FIG. 1 with FIG. 2, it appreciated that the method taught herein reduces the amount of steps, and thus time, to expand a nitinol tube.

Figure 3A:
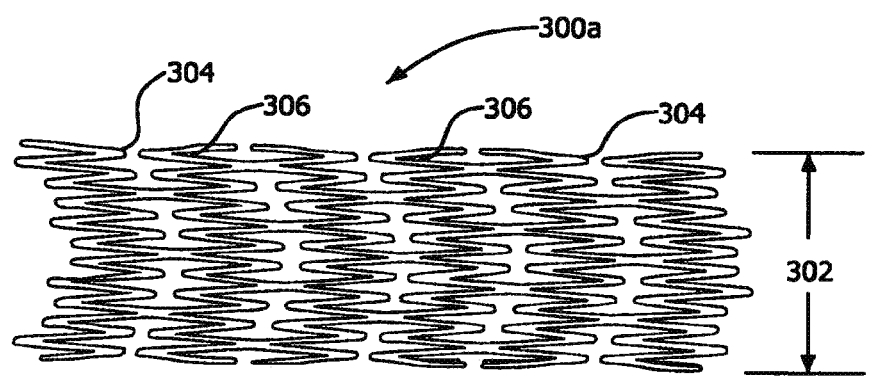
FIGS. 3A and 3B are perspective drawings of a cut patterned tube before and after expansion.
Figure 3B:
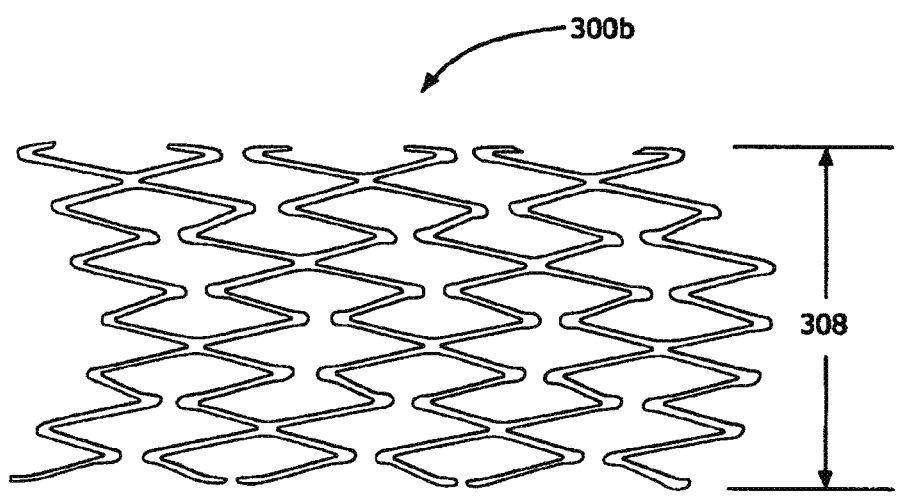

FIG. 3A is a partial perspective view of a typical cut tube 300a, having an initial small diameter 302. The cut tube 300a has an undulating shape, typical of an implantable stent, comprising peaks 304 and valleys 306. FIG. 3B is a partial perspective view of the expanded cut tube 300b after being expanded to a larger diameter 308. The larger diameter 308 is about 100% greater than the initial small diameter 302. The tube 300a can be cut to have any desired pattern. For example the tube 300a can be cut to form individual rings, interconnected rings, open and/or closed cells, or shapes such as a sinusoidal shape, a diamond shape, a U shape, a V shape or an ovaloid shape or any other pattern tailored for a given application. The tube 300a can comprise nitinol or any other similar metal having a shape setting temperature range. Nitinol refers to the family of alloys that include binary nickel-titanium binary shape memory alloys as well as nickel-titanium based alloys including ternary and quaternary additions of alloying elements such as but not limited to iron, niobium, chromium, copper, cobalt, vanadium, platinum, and hafnium. Shape memory alloys include nitinol alloys as well as other alloys that are capable of undergoing a reversible crystallographic phase change such as, but not limited, to AgCd, AuCd, CuAlZn, CuAlNi, CuAlBe, CuSn, NiAl, FePt, FePd, MnCu, and FeMnSi alloy systems.

The tube 300a can have diameters ranging from about 0.5 mm to about 100 mm with a preferred range of about 2 mm to about 40 mm. The tube 300a can have a wall thickness ranging from about 0.05 mm to about 10 mm with a preferred range of about 0.1 mm to about 0.5 mm. The length of tube 300a can range from about 1 mm to about 250 mm. The length of tube 300a can be configured in accordance with any specific application.

Figure 4:
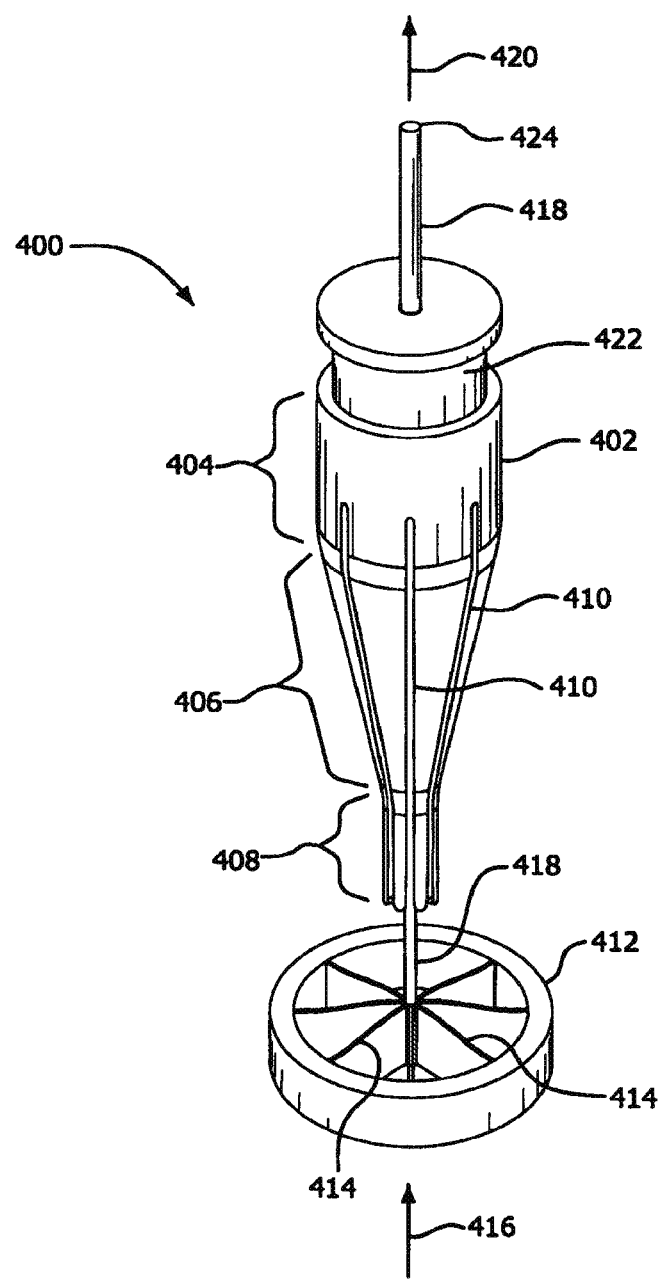
FIG. 4 is a perspective view of an expansion fixture of the present invention, showing a slotted mandrel, expander die, and pull rod.

Shown in FIG. 4 is a perspective view of at least one expansion fixture 400. In this example, the expansion fixture 400 comprises a tapered, slotted, tubular mandrel 402 fabricated from a high temperature metal such as Inconel, stainless steel or other suitable material. The slotted mandrel 402 has a large diameter portion 404, an intermediate tapered portion 406, a small diameter portion 408 and a series of longitudinal slots 410. The longitudinal slots 410 are cut through mandrel wall and extend through the small diameter and tapered portions (408 and 406) of the slotted mandrel. The longitudinal slots 410 are cut through mandrel wall and only partially extend along the large diameter portion 404, as shown in FIG. 4. In an optional configuration, the longitudinal slots can form a spiral. The intermediate tapered portion can optionally have varied taper angles or acute portions in place of a constant taped angle.

The expansion fixture 400 further comprises an expander die 412 having a series of fins 414, as shown in FIG. 4. The fins 414 of the expander die 412 engage with the slots 410 of the slotted mandrel 402 allowing the fins 414 of the expander die to slide through the longitudinal slots 410 of the slotted mandrel 402, along a longitudinal axis as depicted by direction arrow 416.

As further shown in FIG. 4, the expander die 412 is joined to a pull rod 418. The pull rod 418 extends through a center bore of the tubular slotted mandrel 402 and extends out of a collar portion 422 of the slotted mandrel 402. When the pull rod 418 is pulled along a longitudinal axis, depicted by direction arrows 416, 420, the expander die 412 is forced to slide over the small diameter portion 408, the intermediate tapered portion 406 and the large diameter portion 404 of the slotted mandrel 402.

A collar portion 422 of the slotted mandrel 402 is configured to affix the slotted mandrel to a heating source (not shown). The slotted mandrel 402 and expander die 412 are positioned within the heating source. The heating source is configured to allow the end of the pull rod 424 (opposite the expander die) to protrude out of the heating source.

Thus, another embodiment of the invention comprises a device for deforming a shape memory alloy (SMA) article, comprising a slotted elongated tube comprising; i. a longitudinal axis and a first outer perimeter, ii. the tube having a length, a through lumen and a wall, iii. the lumen defining a first inner perimeter, iv. the tube having at least two slots through the wall, v. the slots being oriented essentially parallel to the tube longitudinal axis, vi. the slots extending partially along the tube length; an expansion mandrel comprising, i. a first portion with an essentially constant first perimeter, ii. a second tapered portion, iii. the second tapered portion having a varying perimeter transitioning from the mandrel first perimeter to a larger second perimeter, iv. the mandrel first portion perimeter being dimensioned to be inserted into the lumen first inner perimeter of said slotted elongated tube; and a shape memory alloy article surrounding at least a portion of said slotted elongated tube. In one embodiment, said SMA is nitinol. In another embodiment, said SMA article is a medical device. In another embodiment, said medical device is selected from the group consisting of a stent, cardiac occluder, and an intraluminal filter.

Another embodiment of the invention comprises a device for deforming a shape memory alloy (SMA) article, comprising a slotted elongated tube comprising, i. a longitudinal axis and a first outer perimeter, ii. the tube having a length, a through lumen and a wall, iii. the lumen defining a first inner perimeter, iv. the tube having at least two slots through the wall, v. the slots being oriented essentially parallel to the tube longitudinal axis, vi. the slots extending partially along the tube length; an expansion mandrel comprising, i. a first portion with an essentially constant first perimeter, ii. a second tapered portion, iii. the second tapered portion having a varying perimeter transitioning from the mandrel first perimeter to a larger second perimeter, iv. the mandrel first portion perimeter being dimensioned to be inserted into the lumen first inner perimeter of said slotted elongated tube; wherein the slotted elongated tube surrounds at least a portion of the expansion mandrel and a shape memory alloy article surrounding at least a portion of said slotted elongated tube. In one embodiment, the slotted elongated tube surrounds at least a portion of the expansion mandrel first portion. In another embodiment, the slotted elongated tube surrounds at least a portion of the expansion mandrel second tapered portion. In another embodiment, the expansion mandrel further comprises a third portion having an essentially constant second perimeter. In another embodiment, the slotted elongated tube surrounds at least a portion of the expansion mandrel third portion.

Another embodiment of the invention comprises a device for deforming a shape memory alloy (SMA) article, comprising, a slotted elongated tube comprising, i. a longitudinal axis and a first outer perimeter, ii. the tube having a length, a through lumen and a wall, iii. the lumen defining a first inner perimeter, iv. the tube having at least two slots through the wall, v. the slots being oriented essentially parallel to the tube longitudinal axis, vi. the slots extending partially along the tube length, vii. the tube having a first portion with an essentially constant first perimeter, viii. the tube having a second tapered portion, ix. the second tapered portion having a varying perimeter transitioning from the tube first perimeter to a larger second perimeter; and a translating device comprising, i. a rod sized to extend and slide through the slotted elongate tube through lumen, ii. the rod having at least two fins sized to extend and slide through said slots through the wall of the slotted elongated tube, a SMA article surrounding at least a portion of said slotted elongated tube.

Any suitable heating source can be used to heat the expansion fixture 400, including fluidized baths, salt baths, high temperature liquids, high temperature gasses, radiant heating, inductive heating, convection heating, electrical resistance heating, radio frequency heating, conduction heating or by combinations of different energy sources.

Thus, one embodiment of the invention comprises a process for expanding a cut tube, comprising the steps of: cutting a metallic tube to form a desired cut pattern; placing the cut metallic tube onto a small diameter portion of a slotted tapered mandrel; inserting a pull rod with an attached expander die through a center bore of the slotted tapered mandrel; engaging a series of fins (integral to the expander die) into the slots of the tapered mandrel; placing the cut tube, the slotted tapered mandrel and the expander die into a heating source, so that an end of the pull rod extends out of the heating source; heating the cut tube, the slotted tapered mandrel and the expander die to an elevated temperature (shape setting temperature); translating the pull rod (while maintaining the shape setting temperature of the cut tube, the slotted tapered mandrel and the expander die) to force the expander die to slide over the small diameter portion, a tapered portion and a larger diameter portion of the slotted tapered mandrel, wherein the fins of the expander die engage the cut SMA tube and force the cut SMA tube over the small diameter portion, the tapered portion and the larger diameter portion of the slotted tapered mandrel as the pull rod is translated.

Figure 5C:
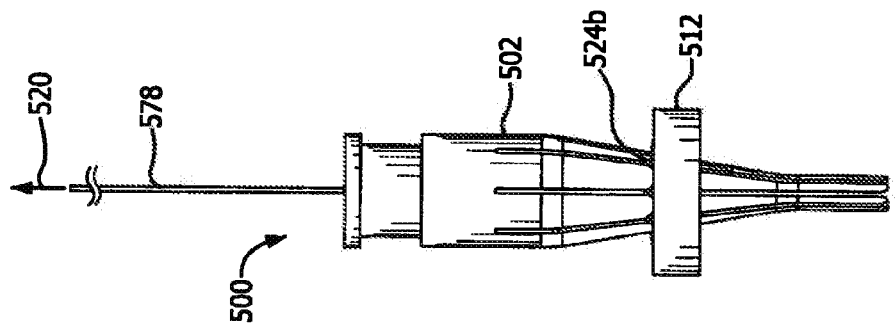
FIG. 5C is a side-view of a stent expansion mandrel assembly of the present invention, showing a slotted mandrel, expander die, pull rod, and a partially expanded stent.
Figure 5B:
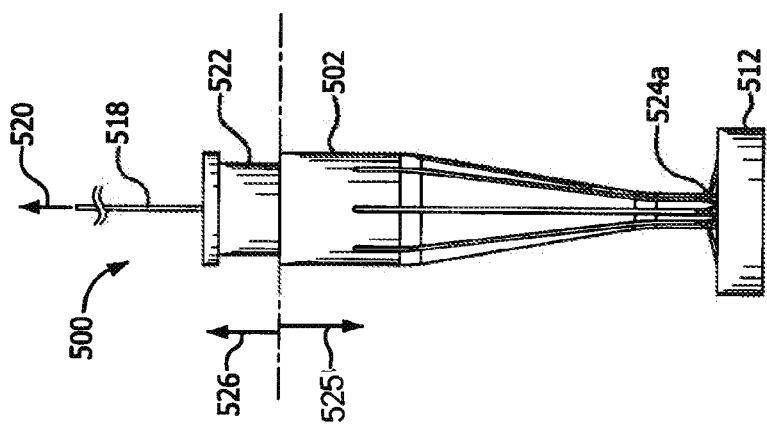
FIG. 5B is a side-view of a stent expansion mandrel assembly of the present invention, showing a slotted mandrel, expander die, pull rod, and a stent.
Figure 5A:
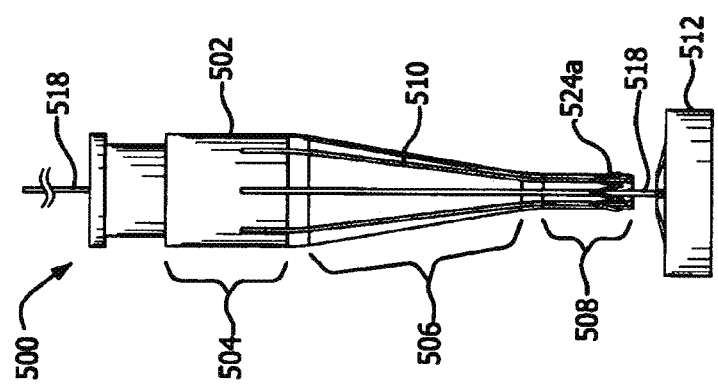
FIG. 5A is a side-view of a stent expansion mandrel assembly of the present invention, showing a slotted mandrel, expander die, pull rod, and stent.

One process for expanding a cut SMA tube according to the present invention is outlined in FIGS. 5A through 5E. Shown in FIG. 5A is an expansion fixture 500. The expansion fixture 500 comprises a tapered, slotted, tubular mandrel 502. The slotted mandrel 502 has a large diameter portion 504, an intermediate tapered portion 506, a small diameter portion 508 and a series of longitudinal slots 510. The longitudinal slots 510 are cut through mandrel wall and extend through the small diameter and tapered portions (508 and 506) of the slotted mandrel. The longitudinal slots 510 are cut through mandrel wall and only partially extend along the large diameter portion 504, as shown in FIG. 5A.

A cut tube 524a having an initial small diameter is placed over the small diameter portion 508 of the slotted mandrel 502.

An expander die 512 having a series of fins (414 of FIG. 4) configured to engage with the slots 510 of the slotted mandrel 502 is joined to a pull rod 518. The pull rod 518 extends through a center bore of the tubular slotted mandrel 502 and extends out of the slotted mandrel end that is opposite of the expander die.

As shown in FIG. 5B, the pull rod 518 is translated in the direction indicated by arrow 520, causing the expander die 512 to advance and allowing the expander die fins (414 of FIG. 4) to engage the slots 510 of the slotted mandrel 502.

The expansion fixture with the cut tube is then put onto a heating chamber (not shown) so that the collar portion 522 and the protruding pull rod 518 are outside of the heated chamber (indicated by direction arrow 526), while the remaining portions of the slotted mandrel 502, expander die 512 and cut tube 524a are exposed to the heated area of the heating chamber (indicated by direction arrow 525). The temperature of the heating chamber is then be elevated to the desired temperature. If a salt bath or similar heat transfer medium is used, the medium can be pre-heated or fully heated to the desired elevated temperature.

As shown in FIG. 5C, after an appropriate dwell within the heated chamber, the pull rod 518 is further advanced along direction 520 causing the expander die 512 to force the cut tube 524b over the tapered portion 506 of the slotted mandrel 502.

Figures 5D, 5E:
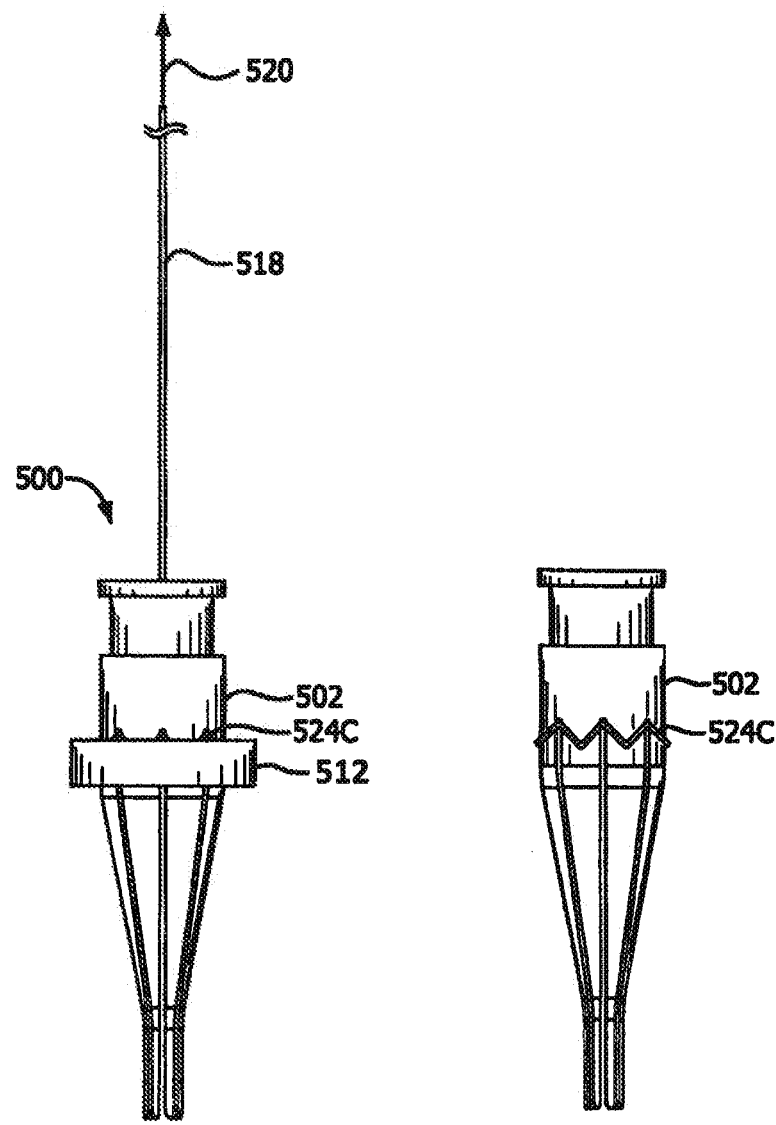
FIG. 5D is a side-view of a stent expansion mandrel assembly of the present invention, showing a slotted mandrel, expander die, pull rod, and a fully expanded stent.
FIG. 5E is a side-view of a stent expansion mandrel assembly of the present invention, showing a slotted mandrel and a fully expanded stent.

As shown in FIG. 5D, the pull rod 518 is further advanced along direction 520 causing the expander die 512 to force the cut tube 524c over the large diameter portion 504 of the slotted mandrel 502. The translation of the pull rod 518 can comprise a continuous motion, an intermittent motion or variable speed motion.

The expansion fixture 500 with the fully expanded cut tube 524c is then removed from the heating chamber. The pull rod 518 and expander die 512 are withdrawn from the slotted mandrel 502. The slotted mandrel 502 and fully expanded cut tube 524c are then quenched in an ambient temperature water bath. After reaching ambient temperature, the fully expanded cut tube 524c can be removed from the slotted mandrel 502.

Although the FIGS. 5A through 5E describe a small length tube, any length of tubing can be expanded using the above process. The large diameter portion 404, 504 of the slotted mandrel 402, 502 can be any size to accommodate any length tube.

The process describe in FIGS. 5A through 5E is one way of using an internal force (internal to the tube to be expanded) to expand a SMA tube, other methods can be used. These include an expanding mandrel that expands a tube laid over said mandrel.

Another embodiment, expansion of a cut SMA tube accomplished by application of an external force, pulling the tube open. Hooks or clamps that grab specific areas of the tube can pull the tube open to expand the tube.

While particular embodiments of the present invention have been illustrated and described herein, the present invention should not be limited to such illustrations and descriptions. It should be apparent that changes and modifications may be incorporated and embodied as part of the present invention within the scope of the following claims. The following examples are further offered to illustrate the present invention.

EXAMPLES

Example 1: Loading and Expanding a Cut Nitinol Tube on a Slotted Mandrel

A nitinol stent ring 524a as illustrated in FIGS. 5A and 5B was obtained. The stent ring 524a was laser cut from a nitinol tube having an inner diameter (ID) of about 4 mm and a wall thickness of about 0.5 mm. The length of the stent ring 524a was about 10 mm.

As shown in FIG. 4, a tapered, slotted mandrel 402 made from a suitable high temperature steel was custom fabricated. The large diameter 404 of the slotted mandrel 402 was about 26 mm. The small diameter 408 of the slotted mandrel 402 was about 8 mm. The length of the slotted mandrel 402 was about 11 cm. An expander die 412 made from a suitable high temperature steel was custom fabricated.

The expander die 412 was designed in such a way that the fins 414 of the die engaged with the slots 410 of the slotted mandrel 402 allowing the expander die 412 to slide through the slotted mandrel 402.

The expander die 412 is attached by such means as laser welding for example to the pull rod 418. The pull rod 418 has a diameter of about 2 mm, a length of about 60 cm, and is fabricated from a suitable high temperature steel. A fluidized bath (Techne Fluidized Bath Model FB-08) used for heat treating parts was obtained.

As shown in FIG. 5A, the stent ring 524a was loaded onto the small diameter 508 of the slotted mandrel 502. In order to load the about 4 mm ID stent ring 524a onto the about 8 mm small diameter 508 end of the slotted mandrel 502, the stent ring 524a was first expanded up to about 8 mm using a tapered mandrel having a diameter of about 4 mm on one end and a diameter of about 8 mm on the opposite end (at room temperature). At this point, the stent is minimally constrained (or substantially unconstrained). The about 8 mm end of the tapered mandrel was then butted up against the about 8 mm small diameter 508 end of the slotted mandrel 502 and the stent ring 524a was transferred from the tapered mandrel to the slotted mandrel 502 at room temperature. The pull rod 518 with attached expander die 512 was inserted through the slotted mandrel as illustrated in FIG. 5A. The fins 414 (FIG. 4) of the expander die 512 were engaged with the slots 510 of the slotted mandrel 502 as illustrated in FIG. 5B.

The assembly of the slotted mandrel 502, stent ring 524a, expander die 512, and pull rod 518 were then submerged into the fluidized bath, pre-heated to a temperature of about 550° C., and allowed to dwell for about three minutes. After about 3 minutes the pull rod 518 was pulled up from the position illustrated in FIG. 5B to the position illustrated in FIG. 5D. It took about two seconds of time to pull the pull rod 518 up from the position illustrated in FIG. 5B to the position illustrated in FIG. 5D. As upward force is applied to the pull rod 518, the fins 414 (FIG. 4) of the attached expander die 512 exert force on the stent ring 524b pulling it up the slotted mandrel 502 as illustrated in FIG. 5C. The orientation of the slots 510 and the fins 414 (FIG. 4) also serve to maintain even diametric expansion of the stent ring 524c as illustrated in FIG. 5D. After about 15 minutes of dwell time in the pre-heated fluidized bath the assembly of the slotted mandrel 502, expanded stent ring 524c, expander die 512, and pull rod 518 were then removed from the fluidized bath and water quenched. The pull rod 518 and attached expander die 512 were then removed from the slotted mandrel 502. The expanded nitinol stent ring 524c and slotted mandrel 502 following heat treatment and shape setting in the fluidized bath are illustrated in FIG. 5E. The resulting nitinol stent ring 524c was expanded and shape set to a diameter of about 26 mm.

Referring to FIG. 4, it should be apparent to those skilled in the art that additional fixtures can be used to interface the stent expanding slotted mandrel 402 with the fluidized bath. To accommodate such fixtures, a collar 422 can be cut in the slotted mandrel 402. This collar 422 can be used to attach additional fixtures that allow for the safe submersion of the mandrel into the heated media of the fluidized bath.

It will be evident to those skilled in the art that various modifications may be made to the present invention. For example, the slotted mandrel 402 as illustrated in FIG. 4 could have four slots 410 instead of eight slots 410. Additionally, the expander die 412 could have four fins 414 instead of eight fins 414. Additionally, the length and the resulting taper angle of the slotted mandrel can be modified. For example, the length of the slotted mandrel 402 could be increased to 20 cm instead of about 11 cm, which may decrease the force required during stent expansion.

Example 2: Expansion of Cut Nitinol Tube without Heating

Referring to FIG. 5A through 5E, using the methods and materials of Example 1, a nitinol stent ring 524a was loaded onto the slotted mandrel 502. The stent ring 524a was then expanded at about room temperature (about 20° C.) by pulling the pull rod 518 up from the position illustrated in FIG. 5B to the position illustrated in FIG. 5D. The assembly of the slotted mandrel 502, stent ring 524c, expander die 512, and pull rod 518 as illustrated in FIG. 5D were then submerged into the fluidized bath pre-heated to a temperature of about 550° C., and allowed to dwell for about 15 minutes.

The assembly of the slotted mandrel 502, stent ring 524c, expander die 512, and pull rod 518 were then removed from the fluidized bath and water quenched. The resulting nitinol stent ring was fractured, having a complete discontinuity in the stent ring.

Example 3: Expansion of a Cut Nitinol Tube Using an Expandable Mandel

An alternate expansion fixture is shown in FIGS. 6A through 6D. The slotted tube 610 illustrated in FIGS. 6A and 6C was made from a suitable high temperature steel and has a length of about 15 cm. The slotted tube has an inner diameter of about 4.2 mm and a wall thickness of about 0.25 mm. The slots 604 cut into the tube and the resulting tube segments 606 are each about 12 cm in length.

As shown in FIG. 6B, a tapered mandrel 618 was made from a suitable high temperature steel and has a length of about 40 cm. The large diameter section 612 has a diameter of about 8 mm and a length of about 8 cm. The small diameter section 616 has a diameter of about 4 mm and a length of about 28 cm. The taper 614 section of the tapered mandrel 618 transitions from a diameter of about 8 mm to a diameter of about 4 mm and has a length of about 4 cm.

A nitinol stent 624 as illustrated in FIG. 6A was obtained. The stent 624 was laser cut from a nitinol tube having an inner diameter (ID) of about 4.1 mm and a wall thickness of about 0.25 mm. The length of the stent was about 60 mm. The stent 624 was loaded onto the slotted tube 610 closer to the slotted end 602 of the slotted tube 610. The small diameter end 616 of the tapered mandrel 618 was then inserted into the slotted end 602 of the slotted tube 610.

A fluidized bath used for heat treating parts was obtained (Techne Fluidized Bath Model FB-08).

Figure 6C:
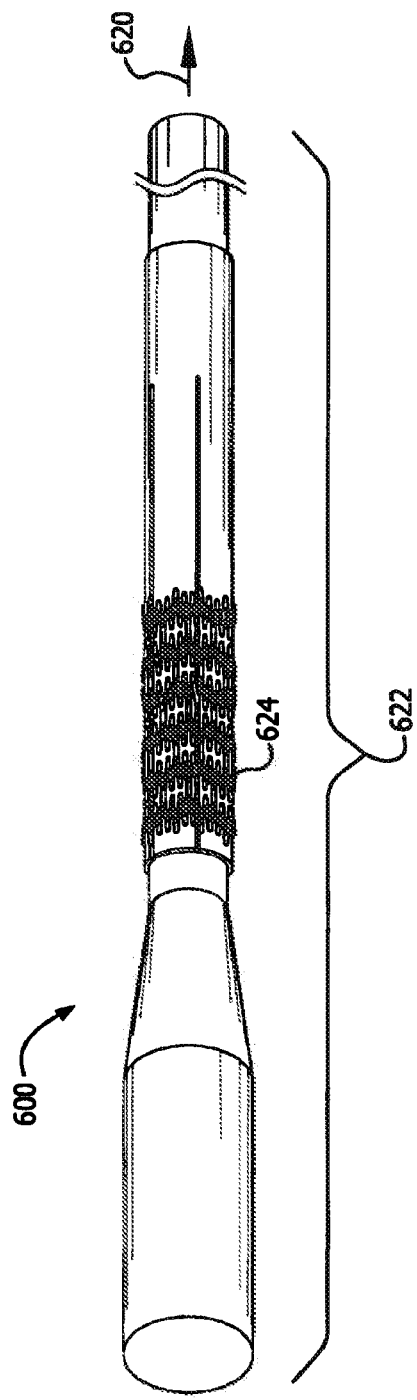
FIG. 6C is a perspective view of a stent expansion mandrel assembly of the present invention, showing a slotted tube, tapered mandrel, and an unexpanded stent.

The assembly of the slotted tube 610, stent 624, and tapered mandrel 618 as illustrated in FIG. 6C was then submerged into the fluidized bath heated to a temperature of about 550° C., and allowed to dwell for about three minutes. After this period of about 3 minutes the tapered mandrel 618 was pulled in the direction 620 illustrated in FIG. 6C to the position illustrated in FIG. 6D. It took about three seconds of time to pull the tapered mandrel 618 from the position illustrated in FIG. 6C to the position illustrated in FIG. 6D.

Figure 6D:
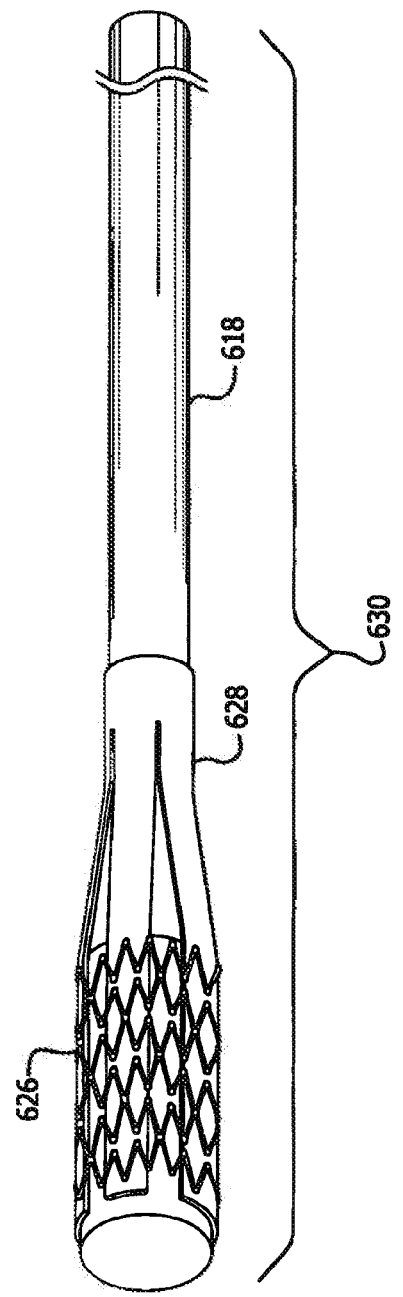
FIG. 6D is a perspective view of a stent expansion mandrel assembly of the present invention, showing a slotted tube, tapered mandrel, and an expanded stent.

After about 15 minutes of dwell time in the pre-heated fluidized bath the assembly of the expanded slotted tube 628, expanded stent 626, and tapered mandrel 618 as illustrated in FIG. 6D were then removed from the fluidized bath and water quenched. The expanded stent 626 was then removed from the expanded slotted tube 628 following heat treatment and shape setting. The resulting nitinol stent was expanded and shape set to a diameter of about 8.5 mm.

It should be apparent to those skilled in the art that additional fixtures can be used to interface the stent expanding hardware illustrated in FIGS. 6A and 6B with the fluidized bath. In addition, it should be apparent to those skilled in the art that the dimensions of the hardware illustrated in FIGS. 6A and 6B may be modified to improve the interface between the stent expanding hardware and the fluidized bath. For example, the length of the small diameter end 616 of the tapered mandrel 618 can be extended further if required to extend safely beyond the level of the heated media of the fluidized bath. Additionally, the length of the uncut end 608 of the slotted tube 610 can be extended further if required to extend safely beyond the level of the heated media of the fluidized bath.

It will be evident to those skilled in the art that various modifications may be made to the present invention. For example, the slotted tube 610 as illustrated in FIG. 6A could have eight slots 604 instead of four slots 604. Additionally, the tapered mandrel 618 could have longitudinal grooves that interface with the segments 606 of the slotted tube 610, which would control the expansion of the segments 606 as they travel up the taper 614 of the tapered mandrel 618.

Example 4: Expansion of a Cut Nitinol Tube Using an Expandable Mandel without a Heat Treatment Using the methods and materials of Example 3, a nitinol stent 624 was loaded onto the slotted tube 610. The stent 624 was then expanded at about room temperature (20° C.) by pulling the tapered mandrel 618 in the direction illustrated in FIG. 6C to the position illustrated in FIG. 6D. The assembly of the slotted tube 610, stent 624, and tapered mandrel 618 as illustrated in FIG. 6C was then submerged into the fluidized bath pre-heated to a temperature of about 550° C. and allowed to dwell for about 15 minutes. The assembly of the expanded slotted tube 628, expanded stent 626, and tapered mandrel 618 as illustrated in FIG. 6D were then removed from the fluidized bath and water quenched. The resulting expanded nitinol stent 626 had multiple fractures.

In addition to being directed to the embodiments described above and claimed below, the present invention is further directed to embodiments having different combinations of the features described above and claimed below. As such, the invention is also directed to other embodiments having any other possible combination of the dependent features claimed below.

Numerous characteristics and advantages of the present invention have been set forth in the preceding description, including preferred and alternate embodiments together with details of the structure and function of the invention. The disclosure is intended as illustrative only and as such is not intended to be exhaustive. It will be evident to those skilled in the art that various modifications may be made, especially in matters of structure, materials, elements, components, shape, size and arrangement of parts within the principals of the invention, to the full extent indicated by the broad, general meaning of the terms in which the appended claims are expressed. To the extent that these various modifications do not depart from the spirit and scope of the appended claims, they are intended to be encompassed therein.

What is claimed is:

1. A method of forming a shape memory alloy (SMA) article, comprising:
   providing a SMA article having an initial shape having an initial size;
   heating the SMA article to a shape setting temperature that is within a range from 300 degrees C. to 650 degrees C.;
   deforming the SMA article in a single step while the SMA article is maintained within the range from 300 degrees C. to 650 degrees C. to a final shape that is at least twice the initial size; and
   cooling the SMA article while the SMA article is being constrained thereby substantially retaining said final shape.

2. The method of claim 1, wherein after deforming said SMA article, allowing said deformed SMA article to dwell at about its shape setting temperature.

3. The method of claim 1, wherein said SMA is nitinol.

4. The method of claim 1, wherein said shape setting temperature is about 300° C. to about 650° C.

5. The method of claim 1, wherein deforming said SMA article into said final shape is accomplished by application of an internal force.

6. The method of claim 1, wherein deforming said SMA article into said final shape is accomplished by application of an external force.

7. The method of claim 1, wherein deforming said SMA article into said final shape is accomplished by use of a tapered mandrel.

8. The method of claim 1, wherein said SMA article is shaped into a medical device.

9. The method of claim 8, wherein said medical device is an implantable medical device.

10. The method of claim 9, wherein said implantable medical device is selected from the group consisting of a stent, cardiac occluder, valve and an intraluminal filter.

11. The method of claim 1, wherein said SMA initial shape was formed by machining.

12. The method of claim 11, wherein said machining comprises laser cutting, water jet cutting, electrical discharge machining, and/or chemical etching.

* * * * *